(12) United States Patent
Panzner et al.

(10) Patent No.: US 7,407,947 B2
(45) Date of Patent: *Aug. 5, 2008

(54) AMPHOTERIC STEROLS AND THE USE THEREOF

(75) Inventors: Steffen Panzner, Halle (DE); Gerold Endert, Halle (DE); Stefan Fankhaenel, Dresden (DE); Nasr El-Mokdad, Halle (DE)

(73) Assignee: Novosom AG, Halle (DE)

( * ) Notice: Subject to any disclaimer, the term of this patent is extended or adjusted under 35 U.S.C. 154(b) by 673 days.

This patent is subject to a terminal disclaimer.

(21) Appl. No.: 10/468,654

(22) PCT Filed: Feb. 21, 2002

(86) PCT No.: PCT/EP02/01878

§ 371 (c)(1),
(2), (4) Date: Feb. 11, 2004

(87) PCT Pub. No.: WO02/066489

PCT Pub. Date: Aug. 29, 2002

(65) Prior Publication Data

US 2004/0120997 A1 Jun. 24, 2004

(30) Foreign Application Priority Data

Feb. 21, 2001 (DE) .................. 101 09 898

(51) Int. Cl.
*A61K 31/58* (2006.01)
*A61K 9/127* (2006.01)
*C07J 43/00* (2006.01)
*C12N 15/00* (2006.01)

(52) U.S. Cl. .................. 514/176; 540/107; 540/108; 540/113; 435/320.1; 424/450

(58) Field of Classification Search .................. 552/107, 552/108, 113; 514/176; 435/320.1; 424/450; 540/107, 108, 113
See application file for complete search history.

(56) References Cited

U.S. PATENT DOCUMENTS

| 4,788,182 A | 11/1988 | Baschang et al. |
| 4,891,208 A | 1/1990 | Janoff et al. |
| 5,888,821 A | 3/1999 | Reszka |
| 5,993,823 A | 11/1999 | Gras-Masse et al. |

FOREIGN PATENT DOCUMENTS

| EP | 0169812 | 1/1986 |
| JP | 02331417 | 11/1990 |
| WO | WO 93/05162 | 3/1993 |
| WO | WO 96/11023 | 4/1996 |
| WO | WO 96/20208 | 7/1996 |
| WO | WO 97/45442 | 12/1997 |
| WO | WO 00/43994 | 10/1998 |
| WO | WO 00/09073 | 2/2000 |
| WO | WO 00/28972 | 5/2000 |
| WO | WO 00/30688 | 6/2000 |
| WO | WO 00/59474 | 10/2000 |
| WO | WO 01/64330 A1 | 9/2001 |

OTHER PUBLICATIONS

Rieko Tachibana et al., *Intracellular Regulation of Macromolecules Using pH-Sensitive Liposomes & Nuclear Localization Signal: Qualitative & Quantitative Evaluation of Intracellular Trafficking*, pp. 538-544, 1998.
S. Band *Handbook of Chemistry and Physics*, 73, 8-37 FF, date needed.
C. Nastruzzi et al., *Liposomes as Carriers for DNA-PNA Hybrids*, Aug. 10, 2000, pp. 237-249.
Toyoaki Ishikura et al., *Preparation of Peptide-Lipid Derivatives and Liposomes Containing the Derivatives*, Aug. 9, 1994.
Ehud M. Landau, *Transfer of Structural Information from Langmuir Monolayers to Three-Dimensional Growing Crystals*, 1985.
A. Pieurdeau et al., *Synthesis of Polymers with Pharmacological Properties. Introduction of Peptide Sequences into the Macromolecular Chain*, 1981.
V. Budker et al., *pH-Sensitive, Cationic Liposomes: A New Synthetic Virus-Like Vector*, Jun. 1996, pp. 760-764.
Ismall M. Hafez et al., *Tunable pH-Sensitive Liposomes Composed of Mixtures of Cationic and Anionic Lipids*, 2000.
Xiao-Jun Li et al., *Theory of Tunable pH Sensitive Vesicles of Anionic and Cationic Lipids or Anionic and Neutral Lipids*, Sep. 22, 2000.
G. Hermanson, *Bioconjugate Techniques*.
Fuxing Tang et al "Introduction of a Disulfide Bond into a Cationic Lipid Enhances Transgene Expression of Plasmid DNA" Department of Pharmaceutics, University of Florida. Received Nov. 26, 1997, Biochemical and Biophysical Research Communications 242, 141-145 (1998).

(Continued)

*Primary Examiner*—Barbara P Badio
(74) *Attorney, Agent, or Firm*—Akerman Senterfitt; Gregory A. Nelson; Gregory M. Lefkowitz

(57) ABSTRACT

An amphoteric compound based on a sterol skeleton, the 3-position of the sterol ring system being substituted by one or more amphoteric groups having an isoelectric point of between about 4 and 9, together with liposomes containing such compounds and their uses.

24 Claims, No Drawings

OTHER PUBLICATIONS

Thomas Fichert et al. "Synthesis and Transfection Properties of Novel Non-Toxic Monocationic Lipids. Variation of Lipid Anchor, Spacer and Head Group Structure." Tumor Biology Center, Department of Clinical Research, Germany. Received Oct. 4, 1999; accepted Feb. 8, 2000, Bioorganic & Medicinal Chemistry Letters 10 (200) 787-791.

AMPHOTERIC STEROLS AND THE USE THEREOF

CROSS REFERENCE TO RELATED APPLICATIONS

This application is a national stage of PCT/EP02/01878 filed Feb. 21, 2002. Priority is claimed from German Patent Application Number 101 09 898.7 filed Feb. 21, 2001.

FIELD OF THE INVENTION

The invention relates to amphoteric compounds based on a sterol skeleton, the 3-position of the ring system being substituted by one or more amphoteric groups with an isoelectric point of between 4 and 9, and to liposomes containing such compounds.

BACKGROUND OF THE INVENTION

The term "lipids" summarizes three classes of natural materials which can be isolated from biological membranes: phospholipids, sphingolipids, and cholesterol, including its derivatives.

These substances are of technical interest in the production of liposomes. Inter alia, such liposomes can be used as containers for active substances in pharmaceutical preparations. In such uses, efficient and stable packaging of the cargo and controllable release of the contents are desirable. Both of these requirements are not easy to combine: the more stable and compact the packaging, the more difficult the release of the entrapped active substance therefrom. For this reason, liposomes changing their properties in response to an external stimulus have been developed. Thermosensitive and pH-sensitive liposomes are well-known. The pH-sensitive liposomes are of special interest, because this parameter undergoes changes even under physiological conditions, e.g. during endocytotic reception of a liposome in a cell, or during passage of the gastrointestinal tract. According to the prior art, pH-sensitive liposomes particularly comprise cholesterol hemisuccinate (CHEMS).

Cholesterol hemisuccinate, in mixture with phosphatidyl ethanolamine, is used to produce pH-sensitive liposomes (Tachibana et al. (1998); BBRC 251, 538-544, U.S. Pat. No. 4,891,208). Such liposomes can enter cells by endocytosis and are capable of transporting cargo molecules into the interior of cells on this route, without doing damage to the integrity of the cellular membrane.

One substantial drawback of CHEMS is its anionic character. Liposomes produced using same have a negative overall charge, being taken up by cells with low efficiency. Despite the transfer mechanism described above, they are barely suitable for the transport of macromolecules into cells.

In WO 00/59474, the prior art describes compounds having a membrane anchor and a cationic and anionic head group, the anionic group being linked to the basic structure via a disulfide bridge. The disulfide bridge can be reduced under physiological conditions, e.g. by contact with the cytosol, the anionic head group then is liberated, and the overall molecule assumes a positive charge, thereby enabling fusion with the cell membrane. The toxicity profile and storage stability of the compounds disclosed in WO 00/59474 are disadvantageous, because cleavage of the disulfide bridges results in free cationic lipids. Disadvantageously, these compounds are known to have a cytotoxic effect.

For the transport of active substances into cells (transfection), the art uses cationic liposomes having a preferably high and constant surface charge. The positive overall charge of such particles leads to electrostatic adherence to cells and subsequently to efficient transport into same. The use of these compounds and of liposomes produced using same remains restricted to in vitro or ex vivo applications, because such positively charged liposomes result in uncontrolled formation of aggregates with serum components.

SUMMARY OF THE INVENTION

The object was therefore to produce new compounds,
i) by means of which active substances can be entrapped in liposomes and released therefrom when changing the pH value;
ii) the presence of which aids to achieve the production of amphoteric liposomes which can be mixed with serum under physiological conditions, with no aggregation taking place; and
iii) by means of which liposomes capable of transporting an entrapped active substance into the interior of cells can be produced.

Another object of the invention was to find a way allowing easy and low-cost production of said compounds and incorporation thereof in high amounts in liposomal membranes.

The object of the invention is accomplished by means of sterol derivatives with an isoelectric point of between 4.5 and 8.5, represented by the general formula Amphoteric substance -Y- spacer -X- sterol, wherein Y and X represent linking groups.

The object of the invention is accomplished by conjugating amphoteric groups to the 3-position of a sterol skeleton. Depending on the amphoteric substance used, compounds are obtained which undergo changes in their charge at a specific pH value and allow incorporation thereof in liposomal membranes in surprisingly high amounts. Ordinary and inexpensive sterols or derivatives thereof can be used as starting compounds.

Situated between the amphoteric substance and the sterol skeleton are the molecule fragments: -Y-spacer -X. For example, the spacer is a lower alkyl residue of linear structure, which has from 0 to 8 C atoms and includes 2 ethylenically unsaturated bonds. The spacer may comprise hydroxyl groups to increase the polarity of the molecule.

DETAILED DESCRIPTION

In the context with this invention, the following abbreviations will be used:

| | |
|---|---|
| CHEMS | Cholesterol hemisuccinate |
| PC | Phosphatidyl choline |
| PE | Phosphatidyl ethanolamine |
| PS | Phosphatidyl serine |
| Hist-Chol | Histidylcholesterol hemisuccinate |

Among the membrane-forming or membrane-bound groups of a biological bilayer membrane, the sterols are of special interest because these compounds, in particular, are available at low cost, involve ordinary chemistry, and allow incorporation in membranes in high amounts without increasing the permeability thereof or even completely destroying their membrane character. However, in order to retain this latter feature, it is important that substitution with a polar molecule be at the 3-position of the sterol.

The overall molecule assumes its pH-dependent charge characteristics by the simultaneous presence of cationic and anionic groups in the "amphoteric substance" molecule portion. More specifically, an amphoteric substance is characterized by the fact that the sum of its charge components will be precisely zero at a particular pH value. This point is referred to as isoelectric point. Above the pI the compound has a negative charge, and below the pI it is to be regarded as a positive cation, the pI of the compounds or sterol derivatives according to the invention ranging between 4.5 and 8.5.

The overall charge of the molecule at a particular pH value of the medium can be calculated as follows:

$$z = \Sigma ni \cdot ((qi-1) + (10^{(pK-pH)}/(1+10^{(pK-pH)})))$$

qi: absolute charge of the ionic group below the pK thereof (e.g. carboxyl=0, single-nitrogen base=1)

ni: number of such groups in the molecule

For example, a compound according to the invention is formed by coupling the amino group of histidine to cholesterol hemisuccinate. At a neutral pH value of 7, the product has a negative charge because the carboxyl function which is present therein is in its fully dissociated form, and the imidazole function only has low charge. At an acid pH value of about 4, the situation is reversed: the carboxyl function now is largely discharged, while the imidazole group is fully protonated, and the overall charge of the molecule therefore is positive.

In a preferred embodiment of the invention, the sterol derivative has an isoelectric point of between 5 and 7.

In another preferred embodiment of the invention, the amphoteric substance has one or more cations with a pKa value of between 4 and 8 and, at the same time, one or more anions with a pKa value of between 3 and 7. An advantageous selection as to type and number of functional groups can be made with reference to the above-mentioned formula.

In particular, it is convenient to use functional groups or molecule fragments as charge carriers, which are in dissociated form in a pH range between 4 and 9. For example, these include phosphoric acid groups, sulfonic acid groups or other strong anions. However, these also include primary, secondary or tertiary amino groups, unless mentioned above. These include quaternary ammonium, amidinium, pyridinium, and guanidino groups.

These fixed charges then can be overcompensated by the variable charges described above. That is, the variable charges are used in excess, for example. One advantage when using fully dissociated groups is their strong polarity. Preferred structural fragments from this group are sulfonic acids, phosphoric acids, primary, secondary or tertiary amines, ammonium compounds, guanidinium compounds, amidinium compounds, or pyridinium compounds linked to the molecule by one of the above-mentioned spacers and coupling groups.

In a particularly preferred fashion, the amphoteric substances can be in the form of complete structural moieties. For example, this is the case with o-, m- or p-aminobenzoic acids, imidazolecarboxylic acid, imidazolediacetic acid, but also nicotinic acid or picolinic acid. In particular, the amphoteric substances can be composed of two charge carriers which both change their charge in the above-mentioned pH range of between 4 and 9. The simultaneously occurring loss of anionic charge and gain of cationic charge results in a change of charge in the overall molecule.

In another preferred embodiment of the invention, the cation comprises an imidazole, piperazine, morpholine, purine, and/or pyrimidine. Other advantageous cations having this property essentially include all the other nitrogen bases. Particularly in those cases where the nitrogen bases are in the form of a ring system, positional isomers advantageously are existing, wherein the linking spacer is substituted to various positions of the organic cation. Conveniently, the pKa values of the organic cation can be influenced via said positional isomerism. The relevant fundamental rules are well-known to those skilled in the art. Alternatively, these effects can be estimated from tabular compilations (Handbook of Chemistry and Physics, Vol. 73, pp. 8-37ff.). Coupling advantageously results in amphiphilic organic cations, e.g. those derived from the following classes of substances:

o-, m-, p-anilines; 2-, 3- or 4-substituted anisidines, toluidines or phenetidines; 2-, 3-, 5-, 6-, 7- or 8-substituted benzimidazoles, 2-, 3-, 4- or 5-substituted imidazoles, 1- or 5-substituted isoquinolines, 2-, 3- or 4-substituted morpholines, 2-, 3- or 4-substituted picolines, 1-, 2- or 3-substituted piperazines, 2-, 5- or 6-modified pterines, 3-, 4-, 5-, 6- or 9-substituted purines, 2- or 3-substituted pyrazines, 3- or 4-substituted pyridazines, 2-, 3- or 4-modified pyridines, 2-, 4-, 5- or 6-substituted pyrimidines, 1-, 2-, 3-, 4-, 5-, 6- or 8-substituted quinolines, 2-, 4- or 5-substituted thiazoles, 2-, 4- or 6-substituted triazines, or derivatives of tyrosine. Particularly preferred are the above-mentioned piperazines, imidazoles and morpholines, purines or pyrimidines. Highly preferred are molecule fragments such as occurring in biological systems, i.e., for example: 4-imidazoles (histamine, histidine itself), 2-, 6- or 9-purines (adenine, guanine, adenosine, or guanosine), 1-, 2- or 4-pyrimidines (uracil, thymine, cytosine, uridine, thymidine, cytidine), or pyridine-3-carboxylic acids. The above-mentioned structural fragments may also have additional substituents. For example, these can be methyl, ethyl, propyl, or isopropyl residues, more preferably in hydroxylated form, including one or two hydroxyl groups. Also, these can be hydroxyl or keto functions in the ring system.

For example, nitrogen bases with preferred pKa values are also formed by single or multiple substitution of the nitrogen atom with lower alkanehydroxyls such as hydroxymethyl or hydroxyethyl groups. Suitable organic bases from this group are e.g. aminopropanediols, triethanolamines, tris(hydroxymethyl)methylamines, bis(hydroxymethyl)methylamines, tris(hydroxyethyl)methylamines, bis(hydroxyethyl)methylamines, or the corresponding substituted ethylamines.

In another advantageous embodiment, the anionic charge carriers are carboxyl groups. Naturally, any carboxylic acid can be used as charge carrier. In particular, these include aliphatic straight-chain or branched carboxylic acids with up to 8 C atoms and 0, 1 or 2 ethylenically unsaturated bonds. Exemplary components of compounds are the carboxyl group itself, acetic acid, bromoacetic acid, chloroacetic acid, acetoacetic acid, propionic acid, acrylic acid, butyric acid, crotonic acid, or higher carboxylic acids bound to the aliphatic chain, dicarboxylic acids such as oxalic acid, malonic acid, succinic acid, maleic acid, fumaric acid, malic acid, tartaric acid, glutaric acid, adipic acid, caprylic acid, pimelic acid, suberic acid, cyclohexanedicarboxylic acid or cyclopentanedicarboxylic acid, mono-esterified or amidated or bound to the aliphatic chain, oligocarboxylic acids such as citric acid, isocitric acid or ethylenediaminetetraacetic acid, mono-esterified or amidated or bound to the aliphatic chain.

Other advantageous components of compounds are glycolic acid, lactic acid, hydroxybutyric acid, malic acid, tartaric acid, aspartic acid, or glutamic acid, alanine, glycine, serine, threonine, asparagine, glutamine, proline, tyrosine, or cysteine, or other amino acids or hydroxy acids bound to the side chain via a heteroatom.

Carboxylic acids with suitable properties can also be found as substituents of aromatic systems, e.g. as benzoic acid, anisic acid, o-, m- or p-hydroxybenzoic acid, as dihydroxybenzoic acid, gallic acid, cinnamic acid, phenylacetic acid, hippuric acid, phthalic acid, terephthalic acid, 2-, 3- or 4-pyridinecarboxylic acid, furancarboxylic acid. Other anionic groups are dissociable hydroxyls or thiols, such as occurring in ascorbic acid, N-substituted alloxan, N-substituted barbituric acid, in veronal, phenol, or as a thiol group.

In a preferred embodiment of the invention, the amphoteric substances are peptides including from 1 to 10 amino acids. In another embodiment, particularly the amino acids histidine, arginine, lysine, glutamic acid, or aspartic acid are used in a particularly preferred fashion to form the amphoteric substance and determine the charge characteristics thereof. Other preferred amino acids are glycine, serine, threonine, glutamine, asparagine, but also cysteine, which contribute to increase the polarity and thus enhance the solubility of the amphoteric substance.

In a preferred embodiment of the invention, the sterols are cholesterol, sitosterol, campesterol, desmosterol, fucosterol, 22-ketosterol, 20-hydroxysterol, stigmasterol, 22-hydroxycholesterol, 25-hydroxycholesterol, lanosterol, 7-dehydrocholesterol, dihydrocholesterol, 19-hydroxycholesterol, 5α-cholest-7-en-3β-ol, 7-hydroxycholesterol, epicholesterol, ergosterol, and/or dehydroergosterol, as well as other related compounds. The sterols used with advantage as starting materials may bear various groups in the 3-position thereof, which groups conveniently allow for ready and stable coupling or optionally assume the function of a spacer. Particularly suitable for direct coupling are the hydroxyl group which is naturally present, but also, the chlorine of sterol chlorides, or the amino group of sterolamines, or the thiol group of thiocholesterol.

In a preferred embodiment of the invention, the linking group X comprises the structures —(C═O)—O—; —(C═O)—NH—; —NH—(C═O)—O—; —(C═O)—S—; —O—; —NH—; —S—; or —CH═N—. Advantageously, the linking group Y may correspond in its structure to the group X, and may additionally comprise the structures —O—(O═C)—; —S—(O═C)—; —NH—(O═C)—; —O—(O═C)—NH—; or —N═CH—. For example, the Y group can be omitted in those cases where the amphoteric substance can be coupled directly to the sterol skeleton, e.g. in the esterification of imidazole-4,5-dicarboxylic acid with cholesterol.

In a preferred embodiment of the invention, the spacer is a lower alkyl residue of linear, branched or cyclic structure, which has from 0 to 8 C atoms and includes 0, 1 or 2 ethylenically unsaturated bonds. The spacer may have hydroxyl groups so as to increase the polarity of the molecule. In particular, the spacer can be a sugar, and advantageously a polyethylene glycol which may comprise up to 20 monomer units.

Methods of performing such coupling reactions are well-known to those skilled in the art and may vary depending on the starting material and coupling component employed. Typical reactions are esterification, amidation, addition of amines to double bonds, etherification, or reductive amination.

Particularly preferred molecules can be produced by amidation of cholesterol hemisuccinate, or by formation of a carbamoyl from cholesterol chloroformate, and also by direct esterification with cholesterol. Particularly preferred amphoteric substances include, for example, the following compounds in Table 1, wherein $R_1$ or $R_2$ represent the lipophilic portion of the amphoteric sterol, and $(\ )_n$ represents other portions of the molecule in the sense of the above-defined spacer.

TABLE 1

| Structure | Description |
|---|---|
| 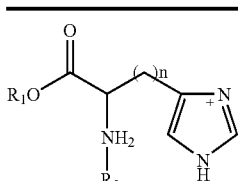 | Histidine derivatives. Coupling of the sterol preferably proceeds via the amino group as $R_2$. In this event, $R_1$ is an anion and can be e.g. H or a hydroxycarboxylic acid or one or more amino acids. Where coupling proceeds via $R_1$, $R_2$ is an anionic residue, e.g. a carboxylic acid or dicarboxylic acid. |
| 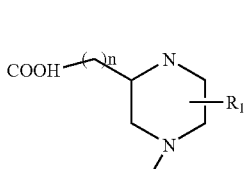 | Piperazine derivatives. Coupling of the sterol may proceed via one of the ring atoms. In those cases where the side chains are hydroxycarboxylic acids or amino acids, coupling may proceed with advantage via these heteroatoms. |
| 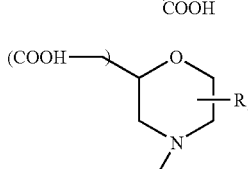 | Morpholine derivatives. Coupling of the sterol may proceed via one of the ring atoms. In those cases where the side chains are hydroxycarboxylic acids or amino acids, coupling may proceed with advantage via these heteroatoms. |
| 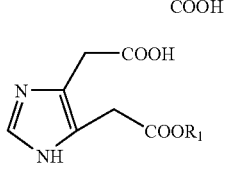 | Derivatives of Imidazole-4,5-diacetic acid. Coupling of the sterol preferably proceeds as an ester via any of the two acetic acid functions. The sterol may also be bound via the 3-amino function. |
| 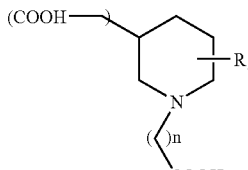 | Piperidine derivatives. Coupling of the sterol may proceed via any of the ring atoms. In those cases where the side chains are hydroxycarboxylic acids or amino acids, coupling may proceed with advantage via their heteroatoms. |
| 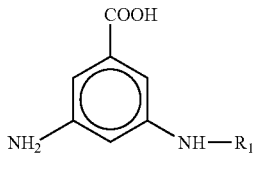 | Diaminobenzoic acid derivatives. Coupling of the sterol preferably proceeds via any of the two amino groups. The second amino group can be alkylated, for example, so as to obtain a higher pKa value. |
| 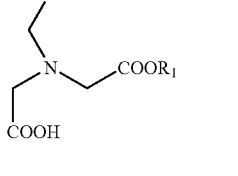 | Nitrilotriacetic acid derivatives. Amphoteric groups are also formed by esterification of nitrilotriacetic acid. In addition, the charge properties of such compounds can be modified by complexing of metal ions. |
| 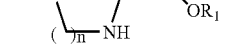 | N-Alkylcarboxyamino acid derivatives. |

TABLE 1-continued

| Structure | Description |
|---|---|
| COOH, COOH, (—)n, COOR₁, (—)m—NH | Amphoteric compounds are also formed by coupling of sterols to the terminal groups of N-acylamino acids. Advantageously, the structure can be derived from serine, aspartic acid or glutamic acid, or from lysine or ornithine. |
| COOH, COOH, (—)n, NR₁, (—)m—NH | Coupling of the aminodicarboxylic acids not only can be at the terminus, but also at the other acid groups. In addition, the charge properties of such compounds can be modified by complexing of metal ions. |
| COOH, COOH, N—N, COOH, COOR₁ | EDTA derivatives. Amphoteric groups are also formed by esterification of ethylenediaminetetraacetic acid. In addition, the charge properties of such compounds can be modified by complexing of metal ions. |

The invention also relates to liposomes comprising the sterol derivatives according to the invention. The compounds of the invention can be incorporated in high amounts in liposomal membranes, resulting in a positive charge of the overall particle only when the pH value of the medium drops below the isoelectric point of the amphoteric substance. Liposomes comprising the components of the invention can be coated with polymers under suitable conditions, where single or multiple deposition of such substances on the surface is possible. In multiple deposition, optionally in the presence of crosslinkers, liposomal nanocapsules are formed as described in WO 00/28972 or WO 01/64330. One advantageous fact when using the substances described herein is that the electrostatic interaction with the polyelectrolyte can be interrupted. As is well-known, the interaction of a polyelectrolyte with charge carriers of the liposomal membrane may give rise to demixing of membrane components and formation of lipid clusters. In many cases, such demixing is accompanied by a permeabilization of the liposomes. The substances of the invention allow for elimination of this interaction following the coating process. When increasing the pH value at this point, the liposomes will be entrapped in the nanocapsules merely in a steric fashion, and interaction between the membrane and polyelectrolytes does no longer exist. In this way, cluster formation of lipids and associated permeabilization of the membrane can be circumvented.

Surprisingly, it has been found that liposomes including the substances of the invention in the membrane thereof readily undergo fusion with other membranes, particularly cell membranes, below the isoelectric point of the substance. In general, this step requires the presence of a larger amount of PE in the membrane. As a result of its tendency of forming hexagonal phases, said PE assumes the function of a helper lipid. However, the inferior stability of such membranes is disadvantageous, and gradual release of entrapped active substances is frequently observed.

Advantageously, liposomes produced using the substances according to the invention undergo effective fusion in the absence of helper lipids. Thus, when using the substances of the invention, it is possible to produce liposomes which are capable of stably encapsulating an active substance, but undergo fusion with cell membranes under the conditions of low pH values to release the active substance there.

This combination of two properties is an important precondition for the incorporation of cargo molecules in cells. In fusion of liposomes with cell envelopes or components, the aqueous volumes of both partners combine, with no opening of the membrane structures to the medium taking place. As a result, uncontrolled influx or efflux of other substances is avoided.

In a preferred embodiment of the invention, the amount of sterol derivative is 50 mole-% at maximum. Compositions comprising at least 2 mole-% of sterol derivatives, but 50 mole-% at maximum, are particularly advantageous. Compositions comprising at least 10 mole-% of sterol derivatives and 40 mole-% at maximum are also preferred. The production of liposomes comprising the substances of the invention proceeds according to techniques well-known to those skilled in the art.

In another preferred embodiment of the invention, the liposomes comprise phosphatidyl choline, phosphatidyl ethanolamine, diacylglycerol, tetraether lipid, and/or PEG lipid. Cholesterols themselves are incapable of forming liposomes, and therefore, addition of further lipid is advantageous. This lipid can be any phospholipid. Obviously, this lipid can also be a ceramide or sphingolipid. It may be convenient to modify the lipid with polyethylene glycol in the polar portion thereof.

In a preferred embodiment of the invention, the liposomes have an average size of between 50 and 1000 nm, preferably between 50 and 300 nm, and more preferably between 60 and 130 nm.

Conveniently, active substances are enclosed in the liposomes, which active substances can be used e.g. in cancer therapy and in the therapy of severe infections. To this end, liposome dispersions can be injected, infused or implanted. Thereafter, they are distributed in the blood or lymph or release their active substance in a controlled fashion as a depot. The latter can be achieved by highly concentrated dispersions in the form of gels. The liposomes can also be used for topical application on the skin. In particular, they may contribute to improved penetration of various active substances into the skin or even passage through the skin and into the body. Furthermore, the liposomes can also be used in gene transfer. Due to its size and charge, genetic material is usually incapable of entering cells without an aid. For this purpose, suitable carriers such as liposomes or lipid complexes are required which, together with the DNA, are to be taken up by the respective cells in an efficient and well-directed fashion. To this end, cell-inherent transport mechanisms such as endocytosis are used. Obviously, the liposomes of the invention can also be used as model membranes. In their principal structure, liposomes are highly similar to cell membranes. Therefore, they can be used as membrane models to quantify the permeation rate of active substances through membranes or the membrane binding of active substances. More advantageously, the active substance is a protein, a peptide, a DNA, RNA, an antisense nucleotide, and/or a decoy nucleotide.

In another preferred embodiment of the invention, at least 80% of the active substance is entrapped in the liposomes. If necessary, non-incorporated cargo molecules adhering on the outside can be removed by simply increasing the pH value. This step is necessary in all those cases where non-incorporated cargo molecules would give rise to aggregation of the liposomes. One advantageous fact when using the components of the invention is that the entrapped active substances must be maintained under conditions allowing interaction with the lipid layer only during the period of actual enclosure. Once the lipid layer remains closed in itself, it is possible to change to other conditions. Thereby, possible inactivation of active substances, particularly of proteins, can be minimized.

The invention also relates to methods of loading liposomes with active substances, using a binding pH value for encapsulation and a second pH value to remove unbound active substances.

Furthermore, the invention relates to a method of loading liposomes with active substances, wherein the liposomes are made permeable at a specific pH value and subsequently sealed. In particular, changes in permeability preferably can be used in a well-directed fashion in loading liposomes. To this end, an active substance to be enclosed can be added to a medium under conditions of high permeability, followed by adjusting conditions of low permeability. In this way, the active substance will remain inside the liposomes. Thereafter, non-entrapped active substance can be removed, if necessary. Such changes in permeability can be induced on liposomes or on liposomal nanocapsules.

The invention also relates to the use of the liposomes in diagnostics and in release systems. Obviously, the liposomes can also be used in a detection system. In particular, the liposomes can be loaded with metal ions whose fluorescence is enhanced by chelate formation, i.e., terbium or europium ions, for example. Liposomes for such uses may of course include components determining the specificity, i.e., antibodies, lectins, selectins, receptors, or hormones, or RNA aptamers. In a particularly preferred embodiment of the use according to the invention, the presence of these metal ions is restricted to the volume of the liposomes so as to avoid non-specific signals from slowly released metal ions adhering on the outside. It is also convenient to use the liposomes in the production of nanocapsules. The liposomes can be used with advantage in the production of release systems in diagnostics. The use for transport and/or release of active substances is also convenient. Advantageously, the liposomes can be used as depot formulation and/or as circulative depot. The use of the liposomes as a vector to transfect cells in vivo, in vitro and/or ex vivo is also advantageous. For example, the liposomes can be used in intravenous and/or peritoneal application.

The sterol derivatives and liposomes according to the invention involve several advantages. Surprisingly, it has been determined that the permeability of the inventive liposomes depends on the pH value and thus, on the state of charge of the sterol derivative. When using Hist-Chol, for example, the liposomes comprising a phosphatidyl ethanolamine are made permeable at a pH value of from 5 to 6 in such a way that entrapped active substances or markers will diffuse out within minutes to hours. In other pH ranges, however, these membranes themselves are stable, showing low initial permeability. Liposomes using the structures according to the invention are therefore particularly suited to construct release systems wherein release of active substances is to proceed in dependence on the pH value of the medium. Surprisingly, it has also been found that amounts of proteins or DNA above average can be enclosed in liposomes including sterol derivatives in the membranes thereof. The efficiency of such incorporation depends on the pH value of the solution employed. Therefore, a process for efficient encapsulation of proteins or DNA in liposomes can be performed by initially adjusting a pH value that would result in good binding of the cargo molecules to the lipid layer. With DNA as polyanion, low pH values of about 4 to 5 are used. With proteins, a useful pH value will depend on the isoelectric point of the protein, which should be below the isoelectric point of the substance according to the invention. Encapsulation is particularly effective when the pH value of the medium is selected so as to range between the isoelectric point of the protein and the isoelectric point of the sterol derivative. The protein then will have a negative and the lipid layer a positive charge.

Surprisingly, it has also been found that liposomes including e.g. Hist-Chol in the membranes thereof are capable of chelating metal ions. This property results in an increase of the positive charge of the liposome. This effect is observed to be particularly strong at neutral pH values, because the inherent charge of the compound is low in this case. Owing to their chelating properties, such liposomes can be used in biochemical diagnostics and in pharmaceutical therapy.

One essential precondition for the use of liposomes for experimental or therapeutic purposes is their compatibility with cells and tissues. A number of well-known compounds used to incorporate DNA or proteins in cells (for example, the cationic lipid DOTAP) are cytotoxic. Surprisingly, it has been found that some of the compounds of the invention exhibit reduced cytotoxicity. In particular, this applies to that group of compounds wherein the amphoteric substance is an amino acid or a peptide. These compounds therefore satisfy one of the preconditions of a transfection system.

Another precondition for the construction of vectors to be used in gene or protein transport into cells is their compatibility with serum or blood. Due to their strong cationic charge, vectors known at present form uncontrollable large aggregates, resulting in formation of thrombi in the organism. Their use in vivo is therefore practically impossible and is restricted to in vitro or ex vivo applications. Surprisingly, it has been found that liposomes constructed using the components of the invention do not form any aggregates in serum or blood. In particular, these are liposomes having an isoelectric point below 7.5.

Another precondition for the construction of vectors to be used in protein or gene transfer is their stability under physiological conditions. Upon application into the blood circulation, liposomes are attacked by components of the complement system and undergo rapid lysis. This reaction proceeds within minutes. As a result, pores are formed in the membrane, which allow even large molecules such as proteins to diffuse out therethrough. At present, stabilization of liposomes with respect to this mechanism is only possible by incorporating cholesterol in the lipid layer. While such liposomes are highly stable, they are no longer able to interact with cells or readily release their active substance. Surprisingly, it has been found that liposomes constructed using the components of the invention can be stable in serum or blood for several hours. Even under such conditions, the release of active substance is low. A liposomal vector for the transport of active substances must satisfy at least three preconditions: it must have low toxicity, entrap the active substance firmly and stably, and be compatible with serum or blood.

Advantageously, all of these three preconditions are satisfied by liposomes produced using selected substances according to the invention. The liposomes are therefore well suited for therapeutic uses. Other properties supporting such uses are good loadability with active substances and well-directed removal of these substances by changing the pH value or by permeabilization of the membrane. Liposomes produced using the substances of the invention show low non-specific binding to cell surfaces. It is this low non-specific binding which is an essential precondition for achieving specific binding to target cells. Target control of the vehicles is obtained when providing the above-described liposomes with additional ligands. As a result, the active substance can be accumulated specifically in such cells or tissues which exhibit a pathological condition.

One important use of the substances according to the invention is therefore in the construction of vectors for transfer of active substances in living organisms. The vectors are particularly suited for the transport of therapeutic macromolecules such as proteins or DNA which themselves are incapable of penetrating the cell membrane or undergo rapid degradation in the bloodstream.

Without intending to be limiting, the invention will be explained in more detail with reference to the following examples.

EXAMPLE 1

Synthesis of Cholesteryl-L-histidyl Succinate (Hist-Chol)

Step I, activation of cholesteryl hemisuccinate: Dicyclohexylcarbodiimide (11.3 mmol; 2.3 g) and 40 ml of THF are placed in a 100 ml flask and cooled to −10° C. Cholesterol hemisuccinate (10.3 mmol; 5 g) and N-hydroxysuccinimide (11.3 mmol; 1.3 g) are added. The mixture is allowed to thaw to RT and stirred for 5 hours. Subsequently, the precipitate having formed (urea) is removed, the filtrate is concentrated, and the residue is recrystallized from ethyl acetate. Colorless needles, m.p.: 145-146° C., 93%.

Step II, cholesteryl-L-histidyl succinate: the activated ester (5.1 mmol; 3 g; step I) is placed in 40 ml of DMF. Sodium hydrogen carbonate (7.6 mmol; 0,6 g) and histidine (7.6 mmol; 1,2 g) are dissolved in 10 ml of water. This solution is added slowly and dropwise to the DMF suspension. This is stirred for 20 hours and subsequently adjusted to pH 4-5 using 2N HCl. The reaction mixture is then concentrated to dryness, and the product is extracted with hot ethanol. Following removal of the ethanol, the product is obtained in pure form. Colorless solid, 78%.

EXAMPLE 2

Preparation of Amphoteric Liposomes 5 mg of Hist-Chol and 9.8 mg of POPC are dissolved in 4 ml of chloroform/methanol (1:1 v/v) and dried completely in a rotary evaporator. The lipid film is hydrated with 4.3 ml of a corresponding buffer (10 mM Kac, 10 mM HEPES, 150 mM NaCl, pH 7.5) at a lipid concentration of 5 mM using ultrasonic treatment for 5 minutes. Finally, the suspension is frozen and, following thawing, subjected to multiple extrusions (Avestine LiposoFast, polycarbonate filter, pore width 200 nm). The profile of the zeta potential in mV at various pH values is illustrated in Table 2 below.

TABLE 2

| pH value | 0 mM NaCl | 100 mM NaCl |
|---|---|---|
| 4.0 | +42 | −20 |
| 5.0 | +28 | +2 |
| 6.0 | −5 | −6 |
| 7.0 | −32 | −15 |
| 8.0 | −45 | −25 |

EXAMPLE 3

Permeability

Lipid films having the composition DMPE/Hist-Chol 60:40 mole- % were prepared in an analogous fashion as in Example 2 and hydrated using 100 mM 6-carboxyfluoresceine (CF), 50 mM NaCl, HEPES 10 mM, pH 8, so as to make a lipid concentration of 25 mM. Non-entrapped CF was removed by gel filtration. For pH- and time-dependent permeability measurements, the liposomes were diluted to 0.2 mM in buffer of the respective pH, and the fluorescence was measured after 30 and 60 minutes, respectively. Thereafter, the temperature was raised to 37° C., and measurement was effected at the same time intervals (30, 60 min). Subsequently, the temperature was raised to 60° C. and again, measurement was effected after 30 and 60 minutes. The percent release of CF is summarized in Table 3 below. Permeabilization is clearly seen at pH 6.5, a value very close to the isoelectric point of Hist-Chol. The membranes are surprisingly stable above and below this pH value.

TABLE 3

|  | 0 min | 30 min | 60 min | 30 min (37° C.) | 60 min (37° C.) | 30 min (60° C.) | 60 min (60° C.) |
|---|---|---|---|---|---|---|---|
| pH 8.0 | 29% | 29% | 28% | 30% | 30% | 36% | 41% |
| pH 7.0 | 32% | 36% | 46% | 39% | 44% | 52% | 60% |
| pH 6.5 | 53% | 70% | 81% | 110% | 132% | 185% | 180% |
| pH 6.0 | 29% | 25% | 26% | 26% | 27% | 30% | 33% |
| pH 5.5 | 28% | 26% | 27% | 26% | 27% | 30% | 32% |
| pH 5.0 | 39% | 41% | 43% | 52% | 61% | 98% | 115% |

EXAMPLE 4

Binding of DNA to Amphoteric Liposomes

For DNA binding, the liposomes comprised of POPC/Hist-Chol 60:40 (mole- %), prepared in $Kac^{10}HEP^{10}NaCl^{100}$, pH 8, according to Example 2, were diluted to 0.2 mM with the buffer to be investigated. DNA (herring DNA, 1 mg/ml standard solution in water) was supplied in appropriate amounts. Subsequently, 0.2 mM liposomes (1 ml) were added. The mixture was rapidly mixed and after 15 minutes, the particle size and zeta potential were determined by dynamic light scattering. With properly selected amount of DNA, the particle size remains nearly unchanged.

At pH values of 7 and 8, where the POPC/Hist-Chol 60:40 liposomes have a negative charge, no change in size or zeta potential could be seen, thus excluding binding of DNA. At pH 4 and 5, the liposomes have a strong positive charge, and DNA binding results in charge exchange of the particles. At pH 6, the liposomes have only weak charge, and a strong negative charge upon addition of DNA. A considerably higher amount of DNA must be added to obtain charge exchange. The zeta potentials and the associated amounts of adsorbed DNA are summarized in Table 4 below:

TABLE 4

| pH value | Zeta potential DNA (mV) | without/with | Adsorbed amount of DNA (µg/mg lipid) |
|---|---|---|---|
| 4 | 41.3 | −37.7 | 15 |
| 5 | 19.6 | −44.7 | 15 |
| 6 | −4.2 | −36.7 | 40 |
| 7 | −36.8 | −35 | — |
| 8 | −52.2 | −52.9 | — |

As can also be deduced from the binding characteristics, removal of non-entrapped DNA adhering on the outside can be achieved by increasing the pH.

EXAMPLE 5

Stability in Human Serum

Liposomes of composition POPC/Hist-Chol 60:40 were prepared as a 5 mM suspension in analogy to Example 2. The serum test was carried out as a dilution series. Varying amounts of liposomes (50-250 µl) were incubated with an equal volume of human serum (250 µl) for 5 minutes at 37° C. (in each case, the total volume was adjusted to 500 µl by addition of 150 mM NaCl). To measure the particle size by means of dynamic light scattering, the mixture was then diluted 1:9 with buffer (KAc10 Hep10 NaCl100; pH 8). The data are summarized in the Table below. The measured particle size approaches the serum value with increasing concentration of the serum. Formation of large aggregates (>1 µm) was not observed (Table 5).

TABLE 5

| Sample<br>250 µl of serum + x µl<br>of liposomes | Particle size<br>(nm) | Polydispersity |
|---|---|---|
| 250 | 94 | 0.574 |
| 125 | 89 | 0.584 |
| 50 | 81 | 0.589 |
| Serum only | 70 | 0.613 |
| Liposomes only | 119 | 0.155 |

EXAMPLE 6

Pharmacokinetics in Blood

500 µl of liposomes comprised of POPC/Chol and POPC/Hist-Chol were administered to male Wistar rats by injection into the tail vein.

50 mM liposome suspensions were prepared by hydrating a lipid film of the respective formulation (addition of 0.03 mole-% of $^{14}$C-DPPC) with 2 ml of a solution of 1 mg of $^3$H-inulin in HEPES 10 mM, NaCl 150 mM, pH 8. Following 3 freeze/thaw cycles, the suspensions were extruded several times through a 400 nm membrane (LiposoFast, Avestin). Removal of non-entrapped $^3$H-inulin was effected by gel filtration over a G-75 Sephadex column and subsequent concentrating over CENTRIPREP (Millipore) centrifugation units. 0.5 ml of liposome suspension was administered to four test animals per formulation, and blood samples were taken after 5 min, 15 min, 60 min, 3 hours, 12 hours, 24 hours. About 50 to 100 mg of the blood samples were dissolved in 1 ml of SOLVABLE tissue dissolver (PACKARD) at 50° C. for 1-3 hours and subsequently decolorized with 0.1-0.5 ml of a 30% hydrogen peroxide solution. Thereafter, 10 ml of scintillator was added, and the activity of $^3$H and $^{14}$C was measured. No direct toxic effects of the compounds could be detected.

Half-life of elimination from blood:

| POPC/Chol | >120 min |
|---|---|
| POPC/Hist-Chol | >90 min |

The invention claimed is:

1. A sterol derivative according to formula (1):

Amphoteric substance -Y- spacer -X- sterol    (1), wherein:

said amphoteric substance comprises a first portion having a cationic charge with a pKa value between about 4 and about 8.5 and a second portion of anionic charge with a pKa value between about 3 and about 7;

said first portion of said amphoteric substance is selected from the group consisting of piperazines, imidazoles, morpholines, purines, and pyrimidines;

said second portion of said amphoteric substance comprises a carboxyl group;

said spacer is a linear or branched $C_{1-8}$ alkyl comprising 0-2 ethylenically unsaturated bonds;

said linking group X is selected from the group consisting of —(C=O)—O—, —(C=O)—NH— and —NH—(C=O)—O—;

said linking group Y is selected from the group consisting of —O—(C=O), —NH—(C=O), —(C=O)—O— and —(C=O)—NH—;

said sterol is selected from the group consisting of cholesterol, sitosterol, campesterol, desmosterol, fucosterol, 22-ketosterol, 20-hydroxysterol, stigmasterol, 22-hydroxycholesterol, 25-hydroxycholesterol, lanosterol, 7-dehydrocholesterol, dihydrocholesterol, 19-hydroxycholesterol, 5α-cholest-7-en-3β-ol, 7-hydroxycholesterol, epicholesterol, ergosterol, and dehydroergosterol; and said sterol derivative has an isoelectric point between about 4.5 and about 8.5.

2. The sterol derivative according to claim 1 wherein said amphoteric substance comprises 1-3 portions of cationic charge and 1-3 portions of anionic charge.

3. The sterol derivative according to claim 1 wherein said sterol derivative has an isoelectric point between about 5 and about 7.

4. The sterol derivative according to claim 1 wherein said amphoteric substance comprises a peptide of 1-10 amino acids, wherein said peptide comprises as a charge carrier one or more amino acids selected from the group consisting of histidine, arginine, lysine, glutamic acid, and aspartic acid.

5. The sterol derivative according to claim 4 wherein the sum of glutamic acid and aspartic acid amino acids of said peptide is greater than the sum of arginine, lysine, and histidine amino acids of said peptide.

6. The sterol derivative according to claim 4 wherein said peptide comprises solely histidine as cationic amino acid, and wherein the sum of glutamic acid amino acids and aspartic acid amino acids is greater than or equal to the number of histidine amino acids.

7. A liposome comprising the sterol derivative of claim 1.

8. The liposome according to claim 7 wherein said liposome comprises less than about 50 mole-% of sterol derivative.

9. The liposome according to claim 8 wherein said liposome comprises between about 2 mole-% and about 50 mole-% of sterol derivative.

10. The liposome according to claim 9 wherein said liposome comprises between about 10 mole-% and about 40 mole-% of sterol derivative.

11. The liposome according to claim 7, wherein the liposome comprises one or more lipids selected from the group consisting of phosphatidyl choline, phosphatidyl ethanolamine, diacylglycerol, tetraether lipid, and PEG lipid.

12. The liposome according to claim 7 wherein said liposome has an average size of between about 50 and about 1000 nm.

13. The liposome according to claim 12 wherein said liposome has an average size of between about 50 and about 300 nm.

14. The liposome according to claim 13 wherein said liposome has an average size of between about 60 and about 130 nm.

15. The liposome according to claim 7 wherein said liposome further comprises an active substance.

16. The liposome according to claim 15 wherein said active substance is selected from the group consisting of a protein, a peptide, a DNA, an RNA, an antisense nucleotide, a decoy nucleotide, and a mixture thereof.

17. The liposome according to claim 15 wherein at least about 80% of said active substance is entrapped inside the liposome.

18. A method of loading the liposome according to claim 15 with said active substance, said method comprising:
encapsulating said active substance in said liposome at a binding pH value; and
removing unbound active substances at a second pH value.

19. A method of loading the liposome according to claim 8 with an active substance, said method comprising:
permeabilizing said liposome by treatment at a pH value sufficient to enable loading of said active substance, and sealing said liposome.

20. A method for the transport and release of an active substance in a subject, said method comprising administering to said subject the liposome of claim 15.

21. The method of claim 20, wherein said administration is intravenous or peritoneal.

22. A depot formulation or circulative depot comprising the liposome of claim 7.

23. A nanocapsule prepared from the liposome of claim 7.

24. A vector for transfecting cells in vivo, in vitro or at vivo, said vector comprising the liposome of claim 7 and a nucleic acid.

* * * * *